(12) United States Patent
Liu et al.

(10) Patent No.: US 11,293,916 B2
(45) Date of Patent: Apr. 5, 2022

US011293916B2

(54) METHOD AND KIT FOR DETECTING CONCENTRATION OF FACTOR H

(71) Applicants: PEKING UNIVERSITY FIRST HOSPITAL, Beijing (CN); Zhongling Liu, Shanghai (CN)

(72) Inventors: Zhongling Liu, Shanghai (CN); Minghui Zhao, Beijing (CN); Feng Yu, Beijing (CN)

(73) Assignees: PEKING UNIVERSITY FIRST HOSPITAL, Shanghai (CN); Zhongling Liu, Shanghai (CN)

( * ) Notice: Subject to any disclaimer, the term of this patent is extended or adjusted under 35 U.S.C. 154(b) by 969 days.

(21) Appl. No.: 16/060,458

(22) PCT Filed: Dec. 9, 2016

(86) PCT No.: PCT/CN2016/109211
§ 371 (c)(1),
(2) Date: Nov. 27, 2018

(87) PCT Pub. No.: WO2017/097255
PCT Pub. Date: Jun. 15, 2017

(65) Prior Publication Data
US 2019/0324021 A1    Oct. 24, 2019

(30) Foreign Application Priority Data

Dec. 11, 2015 (CN) .......................... 201510918917.4
Dec. 11, 2015 (CN) .......................... 201510920358.0

(51) Int. Cl.
*G01N 33/53* (2006.01)
*G01N 33/68* (2006.01)
*G01N 33/543* (2006.01)

(52) U.S. Cl.
CPC ......... *G01N 33/5308* (2013.01); *G01N 33/68* (2013.01); *G01N 33/543* (2013.01)

(58) Field of Classification Search
None
See application file for complete search history.

(56) References Cited

U.S. PATENT DOCUMENTS

| | | | | |
|---|---|---|---|---|
| 7,364,906 | B2 * | 4/2008 | Pankowsky | G01N 33/56966 422/504 |
| 2001/0018072 | A1 * | 8/2001 | Unger | B82Y 5/00 424/484 |
| 2010/0015647 | A1 * | 1/2010 | Amiral | G01N 33/86 435/7.92 |
| 2014/0065726 | A1 * | 3/2014 | Kitahara | C08F 212/08 436/501 |

FOREIGN PATENT DOCUMENTS

| | | |
|---|---|---|
| CN | 102645537 A | 8/2012 |
| CN | 102662059 A | 9/2012 |
| CN | 104049089 A | 9/2014 |
| CN | 104198724 A | 12/2014 |
| CN | 104198725 A | 12/2014 |
| CN | 105388285 A | 3/2016 |
| CN | 105548558 A | 5/2016 |
| WO | 2011017229 A2 | 2/2011 |

OTHER PUBLICATIONS

August et al., Development of a High-Throuput Assay to Measure Histidine Decarboxylase Activity, Journal of Biomolecular Screening 11(7); 2006, pp. 816-821 (Year: 2006).*
Whicher et al., Formulation of optimal conditions for an imunonephelometric assay, Ann Clin Biochem 1980; 17: pp. 170-177. (Year: 1980).*
Lee et al., Improvement of protein stability in protein microarrays, Biotechnology Letters, 2002, 24: pp. 839-844. (Year: 2002).*
International Search Report for PCT/CN2016/109211, dated Mar. 8, 2017.
Sofat, R. et al., "Distribution and Determinants of Circulating Complement Factor H Concentration Determined by a High-Throughput Immunonephelometric Assay", Journal of Immunological Methods, vol. 390, Jan. 30, 2013, pp. 63-73.

* cited by examiner

*Primary Examiner* — Gary Counts
(74) *Attorney, Agent, or Firm* — Greer, Burns & Crain, Ltd.

(57) ABSTRACT

A method comprises adding reagent I to a sample to be detected, incubating to obtain a first detection sample, and detecting to obtain a first absorbance value A1 of the sample to be detected; adding reagent II to the first detection sample, incubating to obtain a second detection sample, and detecting to obtain a second absorbance value A2 of the sample to be detected; adding reagent I to a standard sample, incubating to obtain a first detection standard, and detecting to obtain a first absorbance value B1 of the standard; adding reagent II to the first detection standard, incubating to obtain a second detection standard, and detecting to obtain a second absorbance value B2 of the standard; and using A1 and A2, and B1 and B2 to obtain a concentration level of complement factor H in the sample to be detected.

12 Claims, 4 Drawing Sheets

METHOD AND KIT FOR DETECTING CONCENTRATION OF FACTOR H

This application is a U.S. National Stage under 35 U.S.C. § 371 of International Application No. PCT/CN2016/109211, filed Dec. 9, 2016, which claims priority to Chinese Patent application no. 201510918917.4, filed Dec. 11, 2015, and Chinese Patent application no. 201510920358.0, filed Dec. 11, 2015.

FIELD OF THE INVENTION

The present invention belongs to the field of biological engineering, and particularly relates to a method, a device and a kit for detecting a concentration of a complement factor H.

BACKGROUND OF THE INVENTION

Complement factor H (Factor H) was first discovered and reported by Nilson et al. in 1965, and was named β1f-globulin based on the electrophoretic position (Nilsson, U R and H J Mueller-Eberhard, Isolation of Beta If-Globulin from Human Serum and Its Characterization as the Fifth Component of Complement. J Exp Med, 1965. 122: p. 277-98.), which belongs to the most characteristic member of the complement factor H protein family. The complement factor H family protein gene is located in the region of the 1q32 human complement activation regulatory gene cluster and is a group of glycoprotein in plasma, each consisting of an independently collapsible short consensus repeat (SCR) domain (FIG. 1 and FIG. 2). The complement factor H is a glycoprotein consisting of 1213 amino acid residues with a molecular weight of approximately 150 kDa and consists of 20 SCRs domains, each SCR consists of approximately 60 amino acids which form a globular structure, contains four conserved cysteine residues (I, II, III, IV), with disulfide bonds formed between I-III and II-IV, which help to maintain its spatial conformation. Liver is the main organ for synthesizing the complement factor H, which is also expressed in the mesangial cell and sertoli cell of kidney and renal tubular epithelial cell, retinal pigment epithelium, thrombocyte, peripheral mononuclear cell, neurogliocyte, fibroblast, endotheliocyte, etc. Normal people have rich levels of complement factor H in their blood circulation with a concentration of about 300-800 mg/l, the level of which is affected jointly by heredity and environmental factors, etc.

The different SCR regions of complement factor H can bind to heparin, cell surface mucopolysaccharide, protein components on the surface of microorganism, C-reactive protein (CRP), and complement molecules such as C3b and C3d to exert different physiological functions (FIG. 3). The N-terminal and C-terminal of complement factor H respectively have different biological functions: the SCR1-4 regions at the N-terminal mainly participate in the degradation of the alternative pathway C3 invertase (C3bBb) through the cofactor I in the liquid phase, and can also competitively bind to C3b to inhibit the formation of the C3 invertase (C3bBb); and the C-terminal mainly binds to the mucopolysaccharide on the surface of the host cell, thereby facilitating the SCR1-4 regions at the N-terminal inhibiting the excessive activation of the complement alternative pathway on the surface of the host cell and protecting the host cell from damage. The latest study found that complement factor H can also bind to apoptotic debris, DNA, histone, nucleosome, and annexin-II and other components of apoptotic cells to regulate the removal of the apoptotic cells.

In addition, the complement factor H can also bind to various complement binding proteins on the surface of bacterial, viral, fungal and parasite to mediate bacterial "immune escape"; complement factor H can also bind to cell surface receptors such as CR3, integrin, and L-selectin and the like expressed by neutrophils, B lymphcytes, and monocytes, etc. to mediate cell adhesion and cytokine production to exert immunomodulatory effects.

In recent years, studies have found that the occurrence and development of many cardiovascular diseases, neoplastic diseases, infectious diseases, blood diseases, kidney diseases, rheumatic diseases, ophthalmic diseases, and obstetric diseases, etc. have a certain correlation with the abnormal regulation of complement factor H, that is, the "complement activation regulatory protein region" located on chromosome 1q32 in the potential case may have a genetic abnormality. If the level of complement factor H in the patient's blood can be accurately detected, it can provide help for disease diagnosis, and can indicate the severity of the disease, to guide clinical treatment to a certain extent, and improve patient prognosis.

In the prior art, there are mainly two methods for detecting the level of complement factor H in human circulation, one is enzyme linked immunesorbent assay (ELISA), and the other is radioimmunoassay (RIA). The ELISA method has a long detection time and complicated operation steps; although the radioimmunoassay has a short detection time, radioactive protection is required. Moreover, the two methods can only detect a small amount of samples in single detection, so neither of the two detection methods can quickly and accurately detect the level of complement factor H in batches, and cannot meet the clinical needs.

At present, the immunoturbidimetry used in the field of biological detection is widely used, its basic principle is that: when the antigen reacts with the antibody in a special dilution system and the ratio is appropriate (generally overdosing the antibody), the resulting soluble immune complex precipitates from the liquid phase under the action of an aggregating agent in the diluting system to form micropartibles, causing the reaction liquid to exhibit turbidity. When the antibody concentration is fixed, the amount of immune complex formed increases as the amount of antigen in the sample increases, and the turbidity of the reaction liquid also increases. By measuring the turbidity of the reaction liquid against a series of standards, the antigen content in the detected sample can be calculated. For example, CN101799475 discloses a method for detecting apolipoprotein, which applies the principle of immunoturbidimetry to detect apolipoprotein, in order to achieve the detection of apolipoprotein, it uses "a reagent R1 comprising 5-200 mmol/L buffer, 0.1-10% surfactant, 0.1-40% electrolyte, 20%-80% polymer accelerator, 0.1-0.5% reaction promoter, 0.1-1% stabilizer and appropriate amount of preservative, and balance of purified water, and a reagent R2 with addition of 20-50% anti-human APOE antiserum and 0.001%-5% of the antioxidant in volume ratio in a certain amount of the reagent R1"; for another example, CN102323427A discloses a kit and a method for detecting the concentration of complement C1q in human serum, in the same way, which also applies the principle of immunoturbidimetry to detect the concentration of C1q complement, in order to realize the detection of C1q complement, it uses "a reagent R1 consisting of disodium hydrogen phosphate, monopotassium phosphate, PEG6000, EDTA-Na2, and TX-100", and "a reagent R2 consisting of disodium hydrogen phosphate, monopotassium phosphate, PEG6000, EDTA-Na2, TX-100 and rabbit anti-human complement C1q antiserum".

It can be seen that the above detection methods all use high molecular weight polyethylene glycols, and these methods also need to be combined with various other reagents to achieve the purpose of detection. So, in the prior art, it is still necessary to add different reagents for the detection of different substances by referring to the immunoturbidimetry, so that it is possible to overcome various difficulties in achieving immunoturbidimetric assays, based on this, the inventor has found through a large amount of experimental research that the reagents used in the biological detection achieved by the principle of immunoturbidimetry in the prior art cannot accurately and efficiently realize the concentration detection of complement factor H, moreover, there is currently no report on the use of immunoturbidimetry for the detection of complement factor H, it can be seen that the application of the principle of immunoturbidimetry to achieve the detection of complement factor H still requires a lot of experimentation and verification to overcome the unknown difficulties.

SUMMARY OF THE INVENTION

In order to solve the technical problems existing in the prior art such as long detection time, complicated operation steps, small amount of detected samples in single detection, etc., and that the existing reagents used in the immunoturbidimetry cannot realize the detection of the concentration of complement factor H (Factor H). The present invention utilizes the low-molecular weight polyethylene glycol, adopts the principles of immunity transmission turbidimetry (immunoturbidimetry) and scattered transmission turbidimetry (immunonephelometry) to provide a method that can quickly detect the level of complement factor H in plasma/serum/urine, and can simultaneously detect a large number of samples with simple operation. The method has a wide detection range, a relatively wide requirement for the storage conditions of the samples, requires simple anticoagulation method for the samples and has good clinical application value.

In order to realize the technical purpose of the present invention, the present invention provides a method for detecting the concentration of complement factor H, comprising:

preparing a kit comprising a reagent I and a reagent II containing a complement factor H antibody for detecting the concentration level of complement factor H in a sample to be detected; wherein, the reagent I consists of a Tris buffer and a PEG200 solution, and the reagent II consists of a PEG200 solution and a latex particle suspension of the complement factor H antibody;

adding the reagent I consisting of the Tris buffer and the PEG200 solution to the sample to be detected, incubating to obtain a first detection sample, detecting to obtain a first absorbance value A1 of the sample to be detected; adding the reagent II containing the complement factor H antibody to the first detection sample, incubating to obtain a second detection sample, and detecting to obtain a second absorbance value A2 of the sample to be detected;

adding the reagent I consisting of the Tris buffer and the PEG200 solution to a standard sample, incubating to obtain a first detection standard, detecting to obtain a first absorbance value B1 of the standard; adding the reagent II consisting of the PEG200 solution and the latex particle suspension of the complement factor H antibody to the first detection standard, incubating to obtain a second detection standard, and detecting to obtain a second absorbance value B2 of the standard; and using the resulting first absorbance value A1 and the second absorbance value A2 of the sample to be detected and the first absorbance value B1 and the second absorbance value B2 of the standard sample to obtain the concentration level of the complement factor H in the sample to be detected.

Wherein, the sample to be detected is human plasma, human serum or human urine.

Wherein, the sample to be tested is stored at −80 to 38° C.

Wherein, the test sample is stored for 0-28 days.

Wherein, the concentration of complement factor H in the test sample is 4.68-2000 mg/L.

Wherein, the number of samples to be detected is 500-1000.

Wherein, the concentration of PEG200 in the reagent I is 50-90 g/L, preferably 70 g/L.

Wherein, the concentration of PEG200 in the reagent II is 10-30 g/L, preferably 20 g/L.

In particular, the volume concentration of the latex particle suspension of the complement factor H antibody is 400-800 ml/L, preferably 600 ml/L.

Wherein, the complement factor H antibody is derived from one of a goat anti-human complement factor H antibody, a rabbit anti-human complement factor H antibody or a mouse anti-human complement factor H antibody, and has a titer of 1:64-128.

In particular, the goat anti-human complement factor H antibody, the rabbit anti-human complement factor H antibody, the mouse anti-human complement factor H antibody, a horse anti-human complement factor H antibody or a donkey anti-human or a horse anti-human complement factor H antibody are monoclonal or polyclonal antibodies.

In particular, the PEG200 used for the reagent I or the reagent II can also be replaced with PEG400 or PEG600 or PEG800 or PEG1000.

Wherein, using the resulting first absorbance value A1 and the second absorbance value A2 of the sample to be detected and the first absorbance value B1 and the second absorbance value B2 of the standard sample to obtain the concentration level of the complement factor H in the sample to be detected including:

dividing a difference between the second absorbance value A2 and the first absorbance value A1 of the sample to be detected by a difference between the second absorbance value B2 and the first absorbance value B1 of the standard sample to obtain a ratio K;

multiplying the known concentration of the complement factor H in the standard sample by the obtained ratio K to obtain a concentration value C of the complement factor H in the sample to be detected.

Wherein, the detection conditions set at the time of detection include a temperature of 37° C., a main wavelength of 546 nm or 600 nm, and a sub-wavelength of 700 nm.

In order to realize the technical purpose of the present invention, the present invention further provides a method for detecting the concentration of complement factor H, comprising:

preparing a kit comprising a reagent I and a reagent II for detecting the concentration level of complement factor H in a sample to be detected; wherein, the reagent I consists of Tris buffer and PEG400, and the reagent II consists of Tris buffer, PEG400 and a serum anti-complement factor H antibody;

adding the reagent I consisting of Tris buffer and PEG400 to a sample to be detected, incubating to obtain a first detection sample, and detecting to obtain a first absorbance value A1 of the sample to be detected; adding the reagent II consisting of Tris buffer, serum anti-complement factor H antibody and PEG400 to the first detection sample, incubating to obtain a second detection sample, and detecting to obtain a second absorbance value A2 of the sample to be detected;

adding the reagent I consisting of Tris buffer and PEG400 to a standard sample, incubating to obtain a detection standard sample and detecting to obtain a first absorbance value B1 of the standard sample; adding the reagent II consisting of Tris buffer, serum anti-complement factor H antibody and PEG400 to the first detection standard sample, incubating to obtain a second detection standard sample, and detecting to obtain a second absorbance value B2 of the standard sample; and using the resulting first absorbance value A1 and the second absorbance value A2 of the sample to be detected and the first absorbance value B1 and second absorbance value B2 of the standard sample to obtain the concentration level of complement factor H in the sample to be detected.

Wherein, the sample to be detected is human plasma, human serum or human urine.

Wherein, the storage temperature of the sample to be detected is −80 to 38° C.

Wherein, the storage time of the sample to be detected is 0-28 days.

Wherein, the concentration of complement factor H in the sample to be detected is 4.68-2000 mg/L.

Wherein, the number of samples to be detected is 500-1000.

Wherein, the concentration of PEG400 in the reagent II is 40-80 g/L, preferably 60 g/L.

Wherein, the concentration of PEG400 in the reagent II is 40-80 g/L, preferably 60 g/L.

In particular, the volume concentration of the serum anti-Factor H antibody is 400-800 ml/L, preferably 600 ml/L.

In particular, the PEG400 used for the reagent I or reagent II can also be replaced with PEG200 or PEG600 or PEG800 or PEG1000.

Wherein, using the resulting first absorbance value A1, second absorbance value A2 of the sample to be detected and the first absorbance value B1 and second absorbance value B2 of the standard to obtain the concentration level of complement factor H in the sample to be detected including:

dividing the difference between the second absorbance value A2 and the first absorbance value A1 of the sample to be detected by the difference between the second absorbance value B2 and the first absorbance value B1 of the standard to obtain a ratio K;

multiplying the known concentration of complement factor H in the standard by the obtained ratio K to obtain the concentration value C of complement factor H in the sample to be detected.

Wherein, the detection conditions set at the time of detection are a temperature of 37° C., a main wavelength of 546 nm or 600 nm, and a sub-wavelength of 700 nm.

Wherein, the serum anti-complement factor H antibody is derived from one of goat anti-human Factor H antibody, rabbit anti-human Factor H antibody or mouse anti-human Factor H antibody, and has a titer of 1:64.

Wherein, the goat anti-human Factor H antibody, rabbit anti-human Factor H antibody, mouse anti-human Factor H antibody, horse anti-human Factor H antibody or donkey anti-human or horse anti-human Factor H antibody are monoclonal or polyclonal antibodies.

In order to realize the technical purpose of the present invention, a further aspect of the present invention provides a kit for detecting the concentration of complement factor H, comprising:

a reagent I comprising a Tris buffer and a PEG200 solution; and a reagent II comprising a PEG200 solution and a latex particle suspension of a complement factor H antibody.

Wherein, the concentration of PEG200 in the reagent I is 50-90 g/L; and the concentration of PEG200 in the reagent II is 10-30 g/L.

Wherein, the concentration of the PEG200 solution in the reagent I is 50-90 g/L, preferably 70 g/L.

Wherein, the concentration of the PEG200 solution in the reagent II is 10-30 g/L, preferably 20 g/L.

In particular, the volume concentration of the latex particle suspension of complement factor H antibody is 400-800 ml/L, preferably 600 ml/L.

In particular, the complement factor H antibody is derived from one of goat anti-human complement factor H antibody, rabbit anti-human complement factor H antibody, mouse anti-human complement factor H antibody, horse anti-human complement factor H antibody or donkey anti-human complement factor H antibody, and has a titer of 1:64-128.

Wherein, the goat anti-human complement factor H antibody, rabbit anti-human complement factor H antibody, mouse anti-human complement factor H antibody, horse anti-human complement factor H antibody or donkey anti-human or horse anti-human complement factor H antibody are monoclonal or polyclonal antibodies.

Wherein, the PEG200 used in the reagent I or reagent II can also be replaced with PEG400 or PEG600 or PEG800 or PEG1000.

In particular, the PEG200 solution in the reagent I and reagent II can be replaced with a PEG400 solution, and the latex particle suspension of complement factor H antibody in the reagent II can be replaced with Tris buffer and serum anti-complement factor H antibody.

Wherein, the concentration of the PEG400 solution in the reagent I is 40-80 g/L, preferably 60 g/L.

Wherein, the concentration of the PEG400 solution in the reagent II is 40-80 g/L, preferably 60 g/L.

In particular, the volume concentration of the complement factor H antibody is 400-800 ml/L, preferably 600 ml/L.

In particular, the complement factor H antibody is derived from one of goat anti-human complement factor H antibody, rabbit anti-human complement factor H antibody, mouse anti-human complement factor H antibody, horse anti-human complement factor H antibody or donkey anti-human complement factor H antibody, and has a titer of 1:64-128.

Wherein, the goat anti-human complement factor H antibody, rabbit anti-human complement factor H antibody, mouse anti-human complement factor H antibody, horse anti-human complement factor H antibody or donkey anti-human or horse anti-human complement factor H antibody are monoclonal or polyclonal antibodies.

In particular, the PEG400 used in the reagent I or reagent II can also be replaced with PEG200 or PEG600 or PEG800 or PEG1000.

The advantages of the present invention are that:

1. since the complement factor H is detected using a kit comprising PEG200 or PEG400, the detection has a wide range of sample concentrations and high sensitivity, and the complement factor H with a concentration within the range of 4.86-2000 mg/l can be detected;

2. detection of complement factor H using the method and kit of the present invention has high detection efficiency, and the level of complement factor H in one sample can be detected in 5-10 minutes;

3. the method of the present invention has low requirements for the storage conditions of blood, blood samples with a storage temperature of −80 to 37° C., stored for up to four weeks, or frozen and thawed within 4 cycles can be detected, and the detection result is not affected;

4. the method of the present invention has no anticoagulation requirement for blood, and EDTA or heparin anticoagulant samples can be detected, and the detection result is accurate without being affected; and 5. the method provided by the present invention is simple in operation, can measure the level of complement factor H in human plasma/serum/urine only by detecting the absorbance of the sample to be detected and standard before and after and calculating, thus having low detection cost and high universality.

DETAILED DESCRIPTION OF THE INVENTION

Figure 1:
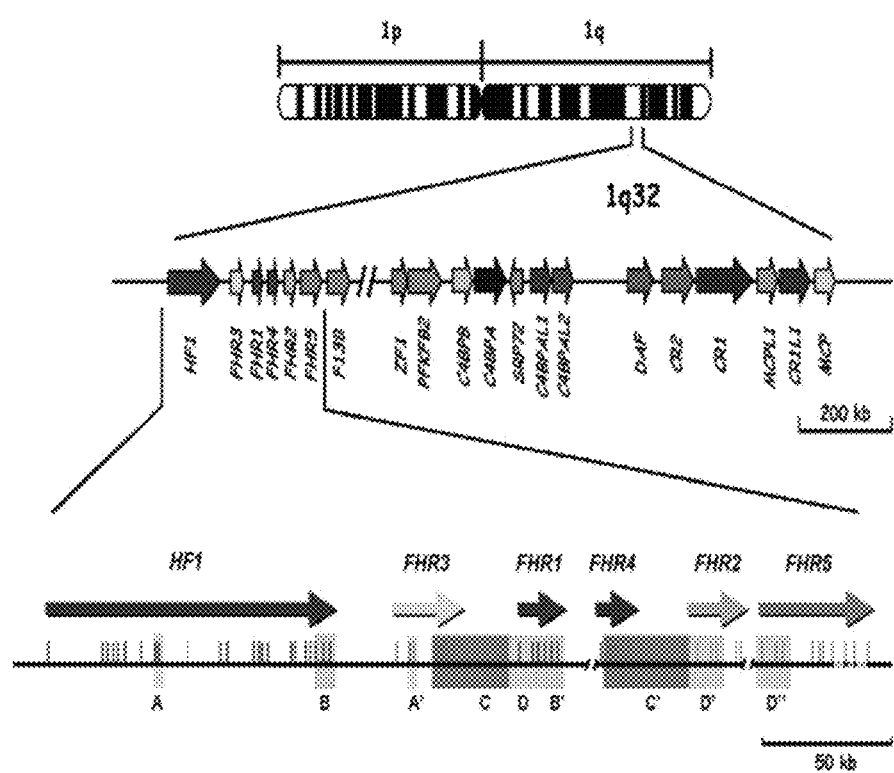
FIG. 1 is a schematic diagram of a gene structure of the complement factor H family described in the background of the present invention.
Figure 2:
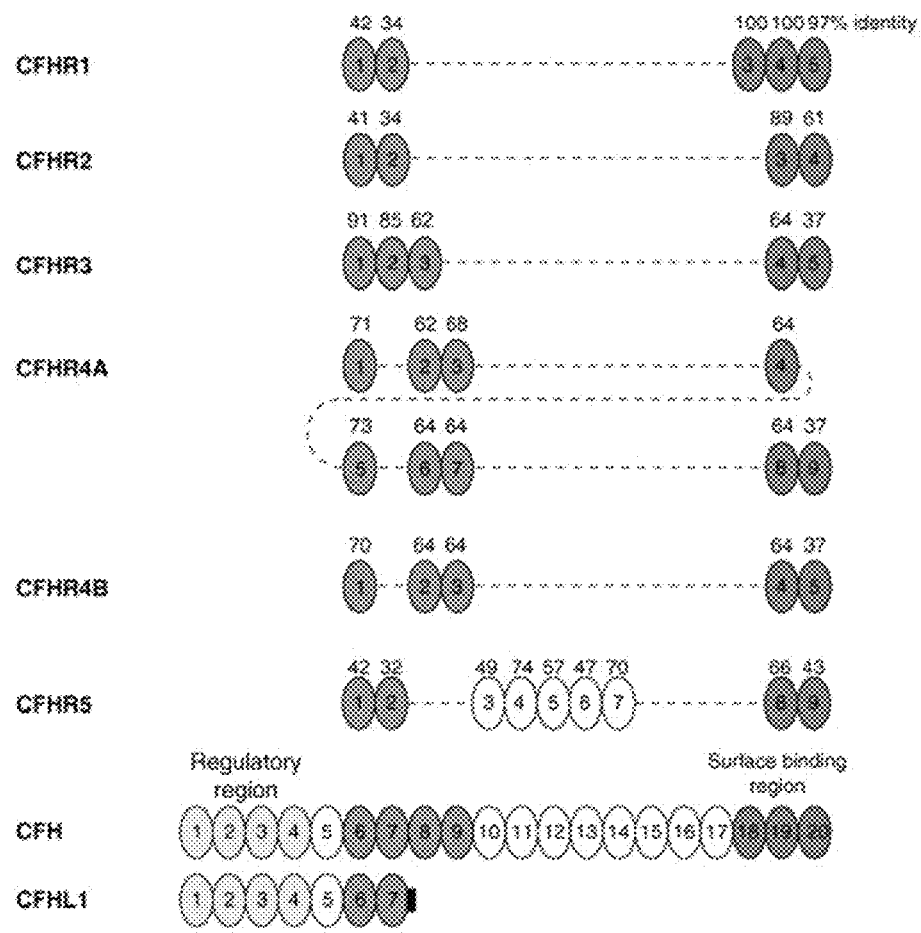
FIG. 2 is a schematic diagram of an SCR structure of the complement factor H family described in the background of the present invention.
Figure 3:
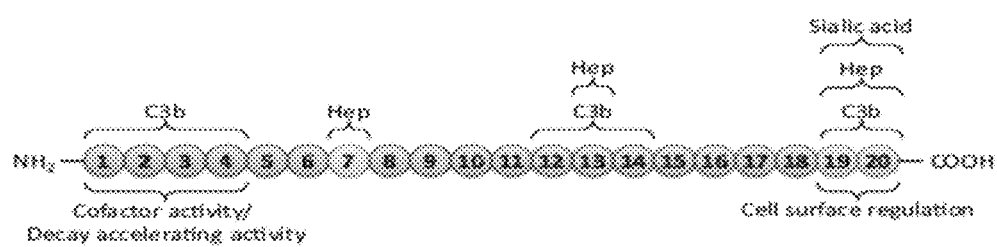
FIG. 3 is a schematic diagram of the binding of complement factor H to various molecules described in the background of the present invention.
Figure 4:
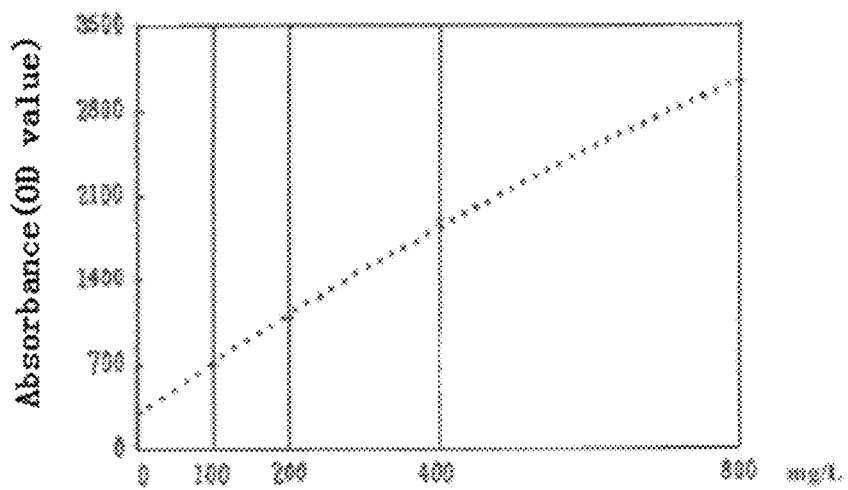
FIG. 4 is a corresponding graph of the concentration of complement factor H and the absorbance OD value described in Example 1 of the present invention.
Figure 5:
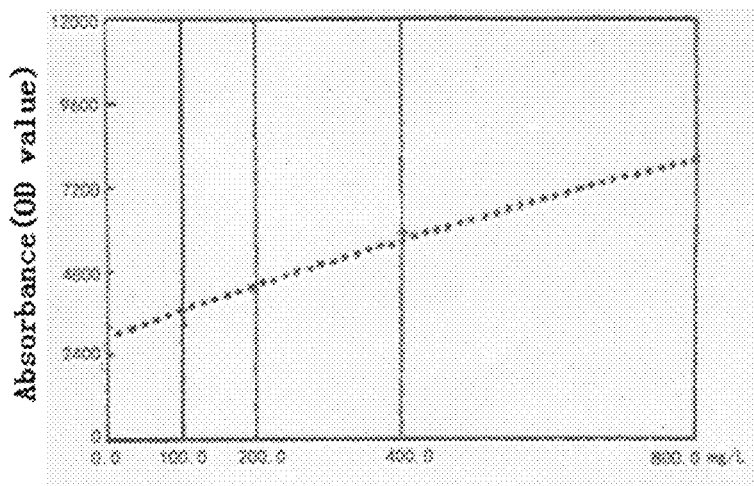
FIG. 5 is a dose response curve of the concentration of Factor H and the absorbance of the standard sample described in Example 4 of the present invention.

The following clearly and completely describes the technical solutions in the embodiments of the present invention with reference to the accompanying drawings in the embodiments of the present invention. It should be noted that the described embodiments are merely some but not all of the embodiments of the present invention. All other embodiments obtained by a person of ordinary skill in the art based on the embodiments of the present invention without creative efforts shall fall within the protection scope of the present invention.

Example 1 Kit

The reagents in the kit were prepared according to the following ratio: Reagent I and Reagent II:

| | |
|---|---|
| Reagent I: | |
| Tris buffer | |
| PEG400 | 60 g/L. |
| Reagent II: | |
| Tris buffer | |
| PEG400 | 60 g/L |
| complement factor H anbody | 600 ml/L. |

The complement factor H antiserum provided by the present invention is one of goat anti-human complement factor H antibody, rabbit anti-human complement factor H antibody, mouse anti-human complement factor H antibody, horse anti-human complement factor H antibody or donkey anti-human complement factor H antibody, and the goat anti-human complement factor H antibody, rabbit anti-human complement factor H antibody, mouse anti-human complement factor H antibody, horse anti-human complement factor H antibody or donkey anti-human complement factor H antibody are monoclonal or polyclonal antibodies.

Example 2 Kit

The reagents in the kit were prepared according to the following ratio: Reagent I and Reagent II:

| | |
|---|---|
| Reagent I: | |
| Tris buffer | |
| PEG400 | 40 g/L. |
| Reagent II: | |
| Tris buffer | |
| PEG400 | 40 g/L |
| complement factor H antiserum | 400 ml/L. |

The complement factor H antibody provided by the present invention is one of goat anti-human complement factor H antibody, rabbit anti-human complement factor H antibody, mouse anti-human complement factor H antibody, horse anti-human complement factor H antibody or donkey anti-human complement factor H antibody, and the goat anti-human complement factor H antibody, rabbit anti-human complement factor H antibody, mouse anti-human complement factor H antibody, horse anti-human complement factor H antibody or donkey anti-human complement factor H antibody are monoclonal or polyclonal antibodies.

Example 3 Kit

The reagents in the kit were prepared according to the following ratio: Reagent I and Reagent II:

| | |
|---|---|
| Reagent I: | |
| Tris buffer | |
| PEG400 | 80 g/L. |
| Reagent II: | |
| Tris buffer | |
| PEG400 | 80 g/L |
| complement factor H antibody | 800 ml/L. |

The complement factor H antibody provided by the present invention is one of goat anti-human complement factor H antibody, rabbit anti-human complement factor H antibody, mouse anti-human complement factor H antibody, horse anti-human complement factor H antibody or donkey anti-human complement factor H antibody, and the goat anti-human complement factor H antibody, rabbit anti-human complement factor H antibody, mouse anti-human complement factor H antibody, horse anti-human complement factor H antibody or donkey anti-human complement factor H antibody are monoclonal or polyclonal antibodies.

Alternatively, the ratio of the above components may also be any of:

| | | | |
|---|---|---|---|
| Reagent I: Tris buffer | PEG400 | 40 g/L | |
| Reagent II: Tris buffer | PEG400 | 40 g/L | |
| | complement factor H antiserum | | 600 ml/L; |
| Reagent I: Tris buffer | PEG400 | 40 g/L | |
| Reagent II: Tris buffer | PEG400 | 40 g/L | |
| | complement factor H antiserum | | 800 ml/L; |
| Reagent I: Tris buffer | PEG400 | 40 g/L | |
| Reagent II: Tris buffer | PEG400 | 60 g/L | |
| | complement factor H antiserum | | 400 ml/L; |
| Reagent I: Tris buffer | PEG400 | 40 g/L | |
| Reagent II: Tris buffer | PEG400 | 60 g/L | |
| | complement factor H antiserum | | 600 ml/L; |
| Reagent I: Tris buffer | PEG400 | 40 g/L | |
| Reagent II: Tris buffer | PEG400 | 60 g/L | |
| | complement factor H antiserum | | 800 ml/L; |
| Reagent I: Tris buffer | PEG400 | 40 g/L | |
| Reagent II: Tris buffer | PEG400 | 80 g/L | |
| | complement factor H antiserum | | 400 ml/L; |
| Reagent I: Tris buffer | PEG400 | 40 g/L | |
| Reagent II: Tris buffer | PEG400 | 80 g/L | |
| | complement factor H antiserum | | 600 ml/L; |
| Reagent I: Tris buffer | PEG400 | 40 g/L | |
| Reagent II: Tris buffer | PEG400 | 80 g/L | |
| | complement factor H antiserum | | 800 ml/L; |
| Reagent I: Tris buffer | PEG400 | 60 g/L | |
| Reagent II: Tris buffer | PEG400 | 40 g/L | |
| | complement factor H antiserum | | 400 ml/L; |
| Reagent I: Tris buffer | PEG400 | 60 g/L | |
| Reagent II: Tris buffer | PEG400 | 40 g/L | |
| | complement factor H antiserum | | 600 ml/L; |
| Reagent I: Tris buffer | PEG400 | 60 g/L | |
| Reagent II: Tris buffer | PEG400 | 40 g/L | |
| | complement factor H antiserum | | 800 ml/L; |
| Reagent I: Tris buffer | PEG400 | 60 g/L | |
| Reagent II: Tris buffer | PEG400 | 60 g/L | |
| | complement factor H antiserum | | 400 ml/L; |
| Reagent I: Tris buffer | PEG400 | 60 g/L | |
| Reagent II: Tris buffer | PEG400 | 60 g/L | |
| | complement factor H antiserum | | 800 ml/L; |
| Reagent I: Tris buffer | PEG400 | 60 g/L | |
| Reagent II: Tris buffer | PEG400 | 80 g/L | |
| | complement factor H antiserum | | 400 ml/L; |
| Reagent I: Tris buffer | PEG400 | 60 g/L | |
| Reagent II: Tris buffer | PEG400 | 80 g/L | |
| | complement factor H antiserum | | 600 ml/L; |
| Reagent I: Tris buffer | PEG400 | 60 g/L | |
| Reagent II: Tris buffer | PEG400 | 80 g/L | |
| | complement factor H antiserum | | 800 ml/L; |
| Reagent I: Tris buffer | PEG400 | 80 g/L | |
| Reagent II: Tris buffer | PEG400 | 40 g/L | |
| | complement factor H antiserum | | 400 ml/L; |
| Reagent I: Tris buffer | PEG400 | 80 g/L | |
| Reagent II: Tris buffer | PEG400 | 40 g/L | |
| | complement factor H antiserum | | 600 ml/L; |
| Reagent I: Tris buffer | PEG400 | 80 g/L | |
| Reagent II: Tris buffer | PEG400 | 40 g/L | |
| | complement factor H antiserum | | 800 ml/L; |
| Reagent I: Tris buffer | PEG400 | 80 g/L | |
| Reagent II: Tris buffer | PEG400 | 60 g/L | |
| | complement factor H antiserum | | 400 ml/L; |
| Reagent I: Tris buffer | PEG400 | 80 g/L | |
| Reagent II: Tris buffer | PEG400 | 60 g/L | |
| | complement factor H antiserum | | 600 ml/L; |
| Reagent I: Tris buffer | PEG400 | 80 g/L | |
| Reagent II: Tris buffer | PEG400 | 60 g/L | |
| | complement factor H antiserum | | 800 ml/L; |
| Reagent I: Tris buffer | PEG400 | 80 g/L | |
| Reagent II: Tris buffer | PEG400 | 80 g/L | |
| | complement factor H antiserum | | 400 ml/L; |
| Reagent I: Tris buffer | PEG400 | 80 g/L | |
| Reagent II: Tris buffer | PEG400 | 80 g/L | |
| | complement factor H antiserum | | 600 ml/L; | the prepared kits have performance close to that of the kit prepared in the preferred embodiment.

In particular, the PEG400 used in the reagent I or reagent II can also be replaced with PEG200 or PEG600 or PEG800 or PEG1000.

Further, the complement factor H anti antibody used in the kit is one of goat anti-human complement factor H antibody, rabbit anti-human complement factor H antibody, mouse anti-human complement factor H antibody, horse anti-human complement factor H antibody or donkey anti-human complement factor H antibody, and the goat anti-human complement factor H antibody, rabbit anti-human complement factor H antibody, mouse anti-human complement factor H antibody, horse anti-human complement factor H antibody or donkey anti-human complement factor H antibody are monoclonal or polyclonal antibodies.

It should be noted that since the liquid PEG 400 is used in the present invention, the reagent I and reagent II provided by the present invention are liquid, therefore, the reagent has high solubility, strong binding ability to the sample to be detected, rapid polymerization acceleration, sufficient and rapid reaction, and the reaction of the sample to be detected can be completed within 2 minutes to obtain the detection result with an accuracy rate of more than 99%.

The reagents prepared by the present invention are suitable for biochemical instruments with different technical specifications, for example:

a kit consisting of one 80 ml-volume reagent I and one 20 ml-volume reagent II can be used for complement factor H concentration detection with a Beckmann Coulter automatic biochemistry analyzer;

a kit consisting of two 60 ml-volume reagents I and two 15 ml-volume reagents II can be used for complement factor H concentration detection with a Hitachi automatic biochemistry analyzer;

a kit consisting of three 67 ml-volume reagents I and two 20 ml-volume reagents II can be used for complement factor H concentration detection with an Olympus automatic biochemistry analyzer;

a kit consisting of four 3.7 ml-volume reagents I and one 3.7 ml-volume reagent II can be used for complement factor H concentration detection with a German Siemens automatic biochemistry analyzer.

Example 4 Kit

The reagents in the kit were prepared according to the following ratio: Reagent I and Reagent II:

| | | |
|---|---|---|
| Reagent I: | | |
| Tris buffer | | |
| PEG200 | 70 g/L. | |
| Reagent II: | | |
| Tris buffer | | |
| PEG200 | 20 g/L | |
| latex particle suspension of complement factor H antibody | | 600 ml/L. |

The complement factor H antibody provided by the present invention is one of goat anti-human complement factor H antibody, rabbit anti-human complement factor H antibody, mouse anti-human complement factor H antibody, horse anti-human complement factor H antibody or donkey anti-human complement factor H antibody, and the goat anti-human complement factor H antibody, rabbit anti-human complement factor H antibody, mouse anti-human complement factor H antibody, horse anti-human complement factor H antibody or donkey anti-human complement factor H antibody are monoclonal or polyclonal antibodies.

Example 5 Kit

The reagents in the kit were prepared according to the following ratio: Reagent I and Reagent II:

| | |
|---|---|
| Reagent I: | |
| Tris buffer | |
| PEG200 | 50 g/L. |
| Reagent II: | |
| Tris buffer | |
| PEG200 | 10 g/L |
| latex particle suspension of complement factor H antibody | 400 ml/L. |

The complement factor H antibody provided by the present invention is one of goat anti-human complement factor H antibody, rabbit anti-human complement factor H antibody, mouse anti-human complement factor H antibody, horse anti-human complement factor H antibody or donkey anti-human complement factor H antibody, and the goat anti-human complement factor H antibody, rabbit anti-human complement factor H antibody, mouse anti-human complement factor H antibody, horse anti-human complement factor H antibody or donkey anti-human complement factor H antibody are monoclonal or polyclonal antibodies.

Example 6 Kit

The reagents in the kit were prepared according to the following ratio: Reagent I and Reagent II:

| | |
|---|---|
| Reagent I: | |
| Tris buffer | |
| PEG200 | 90 g/L. |
| Reagent II: | |
| Tris buffer | |
| PEG200 | 30 g/L |
| latex particle suspension of complement factor H antibody | 800 ml/L. |

The complement factor H antibody provided by the present invention is one of goat anti-human complement factor H antibody, rabbit anti-human complement factor H antibody, mouse anti-human complement factor H antibody, horse anti-human complement factor H antibody or donkey anti-human complement factor H antibody, and the goat anti-human complement factor H antibody, rabbit anti-human complement factor H antibody, mouse anti-human complement factor H antibody, horse anti-human complement factor H antibody or donkey anti-human complement factor H antibody are monoclonal or polyclonal antibodies.

Alternatively, the ratio of the above components may also be any of:

| | | |
|---|---|---|
| Reagent I: Tris buffer | PEG200 | 50 g/L |
| Reagent II: Tris buffer | PEG200 | 10 g/L |
| | latex particle suspension of complement factor H antibody | 400 ml/L; |
| Reagent I: Tris buffer | PEG200 | 50 g/L |
| Reagent II: Tris buffer | PEG200 | 10 g/L |
| | latex particle suspension of complement factor H antibody | 600 ml/L; |
| Reagent I: Tris buffer | PEG200 | 50 g/L |
| Reagent II: Tris buffer | PEG200 | 10 g/L |
| | latex particle suspension of complement factor H antibody | 800 ml/L; |
| Reagent I: Tris buffer | PEG200 | 50 g/L |
| Reagent II: Tris buffer | PEG200 | 20 g/L |
| | latex particle suspension of complement factor H antibody | 400 ml/L; |
| Reagent I: Tris buffer | PEG200 | 50 g/L |
| Reagent II: Tris buffer | PEG200 | 20 g/L |
| | latex particle suspension of complement factor H antibody | 600 ml/L; |
| Reagent I: Tris buffer | PEG200 | 50 g/L |
| Reagent II: Tris buffer | PEG200 | 20 g/L |
| | latex particle suspension of complement factor H antibody | 800 ml/L; |
| Reagent I: Tris buffer | PEG200 | 50 g/L |
| Reagent II: Tris buffer | PEG200 | 30 g/L |
| | latex particle suspension of complement factor H antibody | 400 ml/L; |
| Reagent I: Tris buffer | PEG200 | 50 g/L |
| Reagent II: Tris buffer | PEG200 | 30 g/L |
| | latex particle suspension of complement factor H antibody | 600 ml/L; |
| Reagent I: Tris buffer | PEG200 | 50 g/L |
| Reagent II: Tris buffer | PEG200 | 30 g/L |
| | latex particle suspension of complement factor H antibody | 800 ml/L; |
| Reagent I: Tris buffer | PEG200 | 70 g/L |
| Reagent II: Tris buffer | PEG200 | 10 g/L |
| | latex particle suspension of complement factor H antibody | 400 ml/L; |
| Reagent I: Tris buffer | PEG200 | 70 g/L |
| Reagent II: Tris buffer | PEG200 | 10 g/L |
| | latex particle suspension of complement factor H antibody | 600 ml/L; |
| Reagent I: Tris buffer | PEG200 | 70 g/L |
| Reagent II: Tris buffer | PEG200 | 10 g/L |
| | latex particle suspension of complement factor H antibody | 800 ml/L; |
| Reagent I: Tris buffer | PEG200 | 70 g/L |
| Reagent II: Tris buffer | PEG200 | 20 g/L |
| | latex particle suspension of complement factor H antibody | 400 ml/L; |
| Reagent I: Tris buffer | PEG200 | 70 g/L |
| Reagent II: Tris buffer | PEG200 | 20 g/L |
| | latex particle suspension of complement factor H antibody | 800 ml/L; |

| | | |
|---|---|---|
| Reagent I: Tris buffer | PEG200 | 70 g/L |
| Reagent II: Tris buffer | PEG200 | 30 g/L |
| | latex particle suspension of complement factor H antibody | 400 ml/L; |
| Reagent I: Tris buffer | PEG200 | 70 g/L |
| Reagent II: Tris buffer | PEG200 | 30 g/L |
| | latex particle suspension of complement factor H antibody | 400 ml/L; |
| Reagent I: Tris buffer | PEG200 | 70 g/L |
| Reagent II: Tris buffer | PEG200 | 30 g/L |
| | latex particle suspension of complement factor H antibody | 600 ml/L; |
| Reagent I: Tris buffer | PEG200 | 70 g/L |
| Reagent II: Tris buffer | PEG200 | 30 g/L |
| | latex particle suspension of complement factor H antibody | 800 ml/L; |
| Reagent I: Tris buffer | PEG200 | 90 g/L |
| Reagent II: Tris buffer | PEG200 | 10 g/L |
| | latex particle suspension of complement factor H antibody | 400 ml/L; |
| Reagent I: Tris buffer | PEG200 | 90 g/L |
| Reagent II: Tris buffer | PEG200 | 10 g/L |
| | latex particle suspension of complement factor H antibody | 600 ml/L; |
| Reagent I: Tris buffer | PEG200 | 90 g/L |
| Reagent II: Tris buffer | PEG200 | 10 g/L |
| | latex particle suspension of complement factor H antibody | 800 ml/L; |
| Reagent I: Tris buffer | PEG200 | 90 g/L |
| Reagent II: Tris buffer | PEG200 | 20 g/L |
| | latex particle suspension of complement factor H antibody | 400 ml/L; |
| Reagent I: Tris buffer | PEG200 | 90 g/L |
| Reagent II: Tris buffer | PEG200 | 20 g/L |
| | latex particle suspension of complement factor H antibody | 600 ml/L; |
| Reagent I: Tris buffer | PEG200 | 90 g/L |
| Reagent II: Tris buffer | PEG200 | 20 g/L |
| | latex particle suspension of complement factor H antibody | 800 ml/L; |
| Reagent I: Tris buffer | PEG200 | 90 g/L |
| Reagent II: Tris buffer | PEG200 | 30 g/L |
| | latex particle suspension of complement factor H antibody | 400 ml/L; |
| Reagent I: Tris buffer | PEG200 | 90 g/L |
| Reagent II: Tris buffer | PEG200 | 30 g/L |
| | latex particle suspension of complement factor H antibody | 600 ml/L; | the prepared kits have performance close to that of the kit prepared in the preferred embodiment. In particular, the PEG200 used in the reagent I or reagent II can also be replaced with PEG400 or PEG600 or PEG800 or PEG1000.

Further, the complement factor H antibody used in above-mentioned kit is one of goat anti-human complement factor H antibody, rabbit anti-human complement factor H antibody, mouse anti-human complement factor H antibody, horse anti-human complement factor H antibody or donkey anti-human complement factor H antibody, and the goat anti-human complement factor H antibody, rabbit anti-human complement factor H antibody, mouse anti-human complement factor H antibody, horse anti-human complement factor H antibody or donkey anti-human complement factor H antibody are monoclonal or polyclonal antibodies.

It should be noted that since the liquid PEG200 is used in the present invention, the reagent I and reagent II provided by the present invention are liquid, therefore, the reagent has high solubility, strong binding ability to the sample to be detected, rapid polymerization acceleration, sufficient and rapid reaction, and the reaction of the sample to be detected can be completed within 2 minutes to obtain the detection result with an accuracy rate of more than 99%.

The reagents prepared by the present invention are suitable for biochemical instruments with different technical specifications, for example:

a kit consisting of one 80 ml-volume reagent I and one 20 ml-volume reagent II can be used for complement factor H concentration detection with a Beckmann Coulter automatic biochemistry analyzer;

a kit consisting of two 60 ml-volume reagents I and two 15 ml-volume reagents II can be used for complement factor H concentration detection with a Hitachi automatic biochemistry analyzer;

a kit consisting of three 67 ml-volume reagents I and two 20 ml-volume reagents II can be used for complement factor H concentration detection with a Olympus automatic biochemistry analyzer;

a kit consisting of four 3.7 ml-volume reagents I and one 3.7 ml-volume reagent II can be used for complement factor H concentration detection with a German Siemens automatic biochemistry analyzer.

Test Example 1 Measurement of Kit Performance

The performance of the reagent I and reagent II in the kits prepared in Example 1-3 were evaluated to determine whether the kits complied with the relevant standards of the American Clinical Laboratory Standardization Organization, that is, the CLSI standard.

1. Appearance of Reagent

The reagent I and reagent II in the kits prepared in Example 1-3 were visually observed under light conditions, the reagent I was a colorless clear transparent liquid, and the reagent II was a pale yellow clear liquid, neither has precipitate or impurities, which indicates that the reagents in the kits are normal reagents.

2. Blank Absorbance of Reagent

240 μl of RI (reagent I) of Examples 2-4 were taken, added with 5 μl of distilled water, incubated at 37° C. for 5 min, respectively added with 60 μl of corresponding RII (reagent II), incubated at 37° C. for 5 minutes, and measured on a 7060 automatic biochemistry analyzer at a wavelength of 340 nm. The measured absorbance values of Examples 2-4 were all 0.01, less than 0.04. This indicates that the reagents in the kits are normal blank controls.

3. Determination of Precision 3.1 Test Method for Intra-Batch Precision

Under the normal working conditions of the instrument, using the same batch of reagents, the samples (about 200 mg/L) were continuously tested 20 times, and the mean value ($\overline{X}$) and standard deviation (SD) of the measured values were calculated, then the coefficient of variation (CV %) was calculated according to the following formula. The resulting coefficient of variation was 1.2%, far less than 10%. Therefore, the kit of the present application is stable.

$$(\overline{X}_i)$$

$$SD=\{\Sigma(X_i-\overline{X})^2/(N-1)\}^{1/2}$$

$$i=1$$

$$CV=SD/\overline{X}\times100\%$$

In the formula: SD: standard deviation; CV: coefficient of variation; $\overline{X}$: mean value of the n times measurements; $X_i$ is the ith measured value; N is the number of measurements.

3.2 Test Method for Inter-Batch Precision

Under the normal working conditions of the instrument, three batches of reagents were taken, one for each batch, and each sample (about 200 mg/L) was measured three times. Then the mean values $\overline{X}_1$ $\overline{X}_2$ $\overline{X}_3$ of the measured results of each batch and the total mean value of the measured results of three batches of reagent ($\overline{X}_t$) were calculated. The relative range difference (%) of the mean values of three batch reagents was calculated according to the following formula. The resulting relative range difference was 2.1%, less than 10%. Therefore, the kit of the present application has a good effect.

$$\text{Relative range difference}(\%)=(\overline{X}_{max}-\overline{X}_{min})/\overline{X}_t\times100\%$$

In the formula: $\overline{X}_{max}$ is the maximum value of $\overline{X}_1$, $\overline{X}_2$ and $\overline{X}_3$, and $\overline{X}_{min}$ is the minimum value of $\overline{X}_1$, $\overline{X}_2$ and $\overline{X}_3$.

4. Determination of Accuracy

Under the normal working conditions of the instrument, the reagents were calibrated using the standards provided by the Nephrology Department of the Peking University First Hospital, the sample with known concentration was repeatedly measured 10 times. The relative deviation of the mean value of measurement results was 1.0%. Therefore, the deviation was small and the measurement accuracy was high.

5. Determination of Analysis Sensitivity

To 240 µl of RI reagent, 5 µl of 200 µg/L sample was added, incubated at 37° C. for 5 min, then 60 µl of RII was added, incubated at 37° C. for 5 min, and measured on a 7060 automatic biochemistry analyzer with a wavelength of 340 nm (sub-wavelength 700 nm). The measured absorbance value was 720, less than 0.10. Therefore the kit can sensitively reflect the absorbance of the sample.

6. Determination of Stability

The reagents stored at 2-8° C. under the specified storage conditions until two months before and after the end of the effective period were taken, the blank absorbance, precision, accuracy and analytical sensitivity of which were detected. The resulting blank absorbance was less than 0.10; the coefficient of variation of the intra-assay precision was less than 0.1%, the relative range difference the inter-assay precision was less than 15%; the accuracy was within ±10%; and the analysis sensitivity was greater than 0.04. This product meets the manufacturer's product technical requirements and can be stored at 2-8° C. for at least 12 months, in addition, has a linear correlation of >0.9900, indicating a good linear correlation.

The above determinations were all normal operations, the containers used have been calibrated, the wavelength, sensitivity, and stability of the biochemical analyzer met the requirements, the temperature was accurate, and the distilled water was qualified, and the standard substance content or target value of invariable serum was verified.

It was determined that the kit provided by the present application conforms to the relevant standards of the American Clinical Laboratory Standards Organization, that is, the CLSI standard.

Test Example 2 Detection of Concentration of Complement Factor H Under Different Environmental Conditions The kit provided in Example 1 was used for the detection of concentration of complement factor H in this example.

1. Preparation of Sample 160 fresh blood samples were collected, and the samples were set to the processing groups shown in Table 1 according to the blood storage temperature T, storage time t, and freeze-thaw cycles K, and the concentration of complement factor H in the standard was used as a measurement basis.

TABLE 1

Environmental and Sample Settings

| Sample number | Temperature (° C.) | Storage time (days) | Freeze-thaw cycle |
|---|---|---|---|
| 1 | −80 | 7 | 1 |
| 2 | −80 | 7 | 2 |
| 3 | −80 | 7 | 3 |
| 4 | −80 | 7 | 4 |
| 5 | −80 | 14 | 1 |
| 6 | −80 | 14 | 2 |
| 7 | −80 | 14 | 3 |
| 8 | −80 | 14 | 4 |
| 9 | −80 | 21 | 1 |
| 10 | −80 | 21 | 2 |
| 11 | −80 | 21 | 3 |
| 12 | −80 | 21 | 4 |
| 13 | −80 | 28 | 1 |
| 14 | −80 | 28 | 2 |
| 15 | −80 | 28 | 3 |
| 16 | −80 | 28 | 4 |
| 17 | −40 | 7 | 1 |
| 18 | −40 | 7 | 2 |
| 19 | −40 | 7 | 3 |
| 20 | −40 | 7 | 4 |
| 21 | −40 | 14 | 1 |
| 22 | −40 | 14 | 2 |
| 23 | −40 | 14 | 3 |
| 24 | −40 | 14 | 4 |
| 25 | −40 | 21 | 1 |
| 26 | −40 | 21 | 2 |
| 27 | −40 | 21 | 3 |
| 28 | −40 | 21 | 4 |
| 29 | −40 | 28 | 1 |
| 30 | −40 | 28 | 2 |
| 31 | −40 | 28 | 3 |
| 32 | −40 | 28 | 4 |
| 33 | −20 | 7 | 1 |
| 34 | −20 | 7 | 2 |
| 35 | −20 | 7 | 3 |
| 36 | −20 | 7 | 4 |
| 37 | −20 | 14 | 1 |
| 38 | −20 | 14 | 2 |
| 39 | −20 | 14 | 3 |
| 40 | −20 | 14 | 4 |
| 41 | −20 | 21 | 1 |
| 42 | −20 | 21 | 2 |
| 43 | −20 | 21 | 3 |
| 44 | −20 | 21 | 4 |

TABLE 1-continued

Environmental and Sample Settings

| Sample number | Temperature (° C.) | Storage time (days) | Freeze-thaw cycle |
|---|---|---|---|
| 45 | −20 | 28 | 1 |
| 46 | −20 | 28 | 2 |
| 47 | −20 | 28 | 3 |
| 48 | −20 | 28 | 4 |
| 49 | −10 | 7 | 1 |
| 50 | −10 | 7 | 2 |
| 51 | −10 | 7 | 3 |
| 52 | −10 | 7 | 4 |
| 53 | −10 | 14 | 1 |
| 54 | −10 | 14 | 2 |
| 55 | −10 | 14 | 3 |
| 56 | −10 | 14 | 4 |
| 57 | −10 | 21 | 1 |
| 58 | −10 | 21 | 2 |
| 59 | −10 | 21 | 3 |
| 60 | −10 | 21 | 4 |
| 61 | −10 | 28 | 1 |
| 62 | −10 | 28 | 2 |
| 63 | −10 | 28 | 3 |
| 64 | −10 | 28 | 4 |
| 65 | 0 | 7 | 1 |
| 66 | 0 | 7 | 2 |
| 67 | 0 | 7 | 3 |
| 68 | 0 | 7 | 4 |
| 69 | 0 | 14 | 1 |
| 70 | 0 | 14 | 2 |
| 71 | 0 | 14 | 3 |
| 72 | 0 | 14 | 4 |
| 73 | 0 | 21 | 1 |
| 74 | 0 | 21 | 2 |
| 75 | 0 | 21 | 3 |
| 76 | 0 | 21 | 4 |
| 77 | 0 | 28 | 1 |
| 78 | 0 | 28 | 2 |
| 79 | 0 | 28 | 3 |
| 80 | 0 | 28 | 4 |
| 81 | 5 | 7 | 1 |
| 82 | 5 | 7 | 2 |
| 83 | 5 | 7 | 3 |
| 84 | 5 | 7 | 4 |
| 85 | 5 | 14 | 1 |
| 86 | 5 | 14 | 2 |
| 87 | 5 | 14 | 3 |
| 88 | 5 | 14 | 4 |
| 89 | 5 | 21 | 1 |
| 90 | 5 | 21 | 2 |
| 91 | 5 | 21 | 3 |
| 92 | 5 | 21 | 4 |
| 93 | 5 | 28 | 1 |
| 94 | 5 | 28 | 2 |
| 95 | 5 | 28 | 3 |
| 96 | 5 | 28 | 4 |
| 97 | 10 | 7 | 1 |
| 98 | 10 | 7 | 2 |
| 99 | 10 | 7 | 3 |
| 100 | 10 | 7 | 4 |
| 101 | 10 | 14 | 1 |
| 102 | 10 | 14 | 2 |
| 103 | 10 | 14 | 3 |
| 104 | 10 | 14 | 4 |
| 105 | 10 | 21 | 1 |
| 106 | 10 | 21 | 2 |
| 107 | 10 | 21 | 3 |
| 108 | 10 | 21 | 4 |
| 109 | 10 | 28 | 1 |
| 110 | 10 | 28 | 2 |
| 111 | 10 | 28 | 3 |
| 112 | 10 | 28 | 4 |
| 113 | 20 | 7 | 1 |
| 114 | 20 | 7 | 2 |
| 115 | 20 | 7 | 3 |
| 116 | 20 | 7 | 4 |
| 117 | 20 | 14 | 1 |
| 118 | 20 | 14 | 2 |
| 119 | 20 | 14 | 3 |
| 120 | 20 | 14 | 4 |
| 121 | 20 | 21 | 1 |
| 122 | 20 | 21 | 2 |
| 123 | 20 | 21 | 3 |
| 124 | 20 | 21 | 4 |
| 125 | 20 | 28 | 1 |
| 126 | 20 | 28 | 2 |
| 127 | 20 | 28 | 3 |
| 128 | 20 | 28 | 4 |
| 129 | 30 | 7 | 1 |
| 130 | 30 | 7 | 2 |
| 131 | 30 | 7 | 3 |
| 132 | 30 | 7 | 4 |
| 133 | 30 | 14 | 1 |
| 134 | 30 | 14 | 2 |
| 135 | 30 | 14 | 3 |
| 136 | 30 | 14 | 4 |
| 137 | 30 | 21 | 1 |
| 138 | 30 | 21 | 2 |
| 139 | 30 | 21 | 3 |
| 140 | 30 | 21 | 4 |
| 141 | 30 | 28 | 1 |
| 142 | 30 | 28 | 2 |
| 143 | 30 | 28 | 3 |
| 144 | 30 | 28 | 4 |
| 145 | 37 | 7 | 1 |
| 146 | 37 | 7 | 2 |
| 147 | 37 | 7 | 3 |
| 148 | 37 | 7 | 4 |
| 149 | 37 | 14 | 1 |
| 150 | 37 | 14 | 2 |
| 151 | 37 | 14 | 3 |
| 152 | 37 | 14 | 4 |
| 153 | 37 | 21 | 1 |
| 154 | 37 | 21 | 2 |
| 155 | 37 | 21 | 3 |
| 156 | 37 | 21 | 4 |
| 157 | 37 | 28 | 1 |
| 158 | 37 | 28 | 2 |
| 159 | 37 | 28 | 3 |
| 160 | 37 | 28 | 4 |

2. Sample Processing and Detecting

Sample processing and detecting was performed under the conditions of temperature environment of 15-35° C. and humidity environment of 45-85% using a biochemical analyzer.

That is: 240 μl of the reagent I solution prepared in Example 2 was added to 5 μl of the sample, the resulting mixture was incubated in a biochemical analyzer at 37° C. for 5 minutes, and then measured for its absorbance value A1 at a main wavelength of 340 nm and a sub-wavelength of 700 nm, after the measurement, the reagent II solution containing complement factor H antiserum prepared in Example 2 was added to the sample, the resulting mixture was incubated in a biochemical analyzer at 37° C. for 5 minutes, after an immunoreaction, measured for its absorbance value A2 at a main wavelength of 340 nm and a sub-wavelength of 700 nm. According to the absorbance values of the sample before and after the reaction, the difference A was obtained, ie, A=A2−A1.

3. Calculation of Concentration of Complement Factor H 3.1 Processing and Determination of Standard Sample The operation conditions were the same as in step 2, that is, 240 μl of the reagent I solution prepared in Example 2 was added to 5 μl of the standard sample solution, the resulting mixture was incubated in a biochemical analyzer at 37° C. for 5 minutes, and then measured for its absorbance value B1 at a main wavelength of 340 nm and a sub-wavelength of 700 nm after incubation at 37° C. for 5 minutes in a biochemical analyzer, after the measurement, the reagent II solution containing complement factor H antiserum prepared in Example 2 was added to the standard, the resulting mixture was incubated in a biochemical analyzer at 37° C. for 5 minutes, after the immunoreaction, measured for its absorbance value B2 at a main wavelength of 340 nm and a sub-wavelength of 700 nm. According to the absorbance values of the standard sample before and after the reaction, the difference B was obtained, ie, B=B2−B1.

3.2 Calculation of Concentration of Complement Factor H

According to the difference A of the tested sample between before and after the reaction, the difference B of the standard sample between before and after reaction, and the concentration c (mg/L) of the standard sample, the concentration C (mg/L) of complement factor H was calculated, ie: C=A/B·c, the concentration of complement factor H in the sample was obtained.

According to the result values of the concentration of complement factor H, the analysis results were obtained as shown in Table 2 and Table 3.

TABLE 2

Analysis Result I of Concentration Value of Complement Factor H

| Comparative value | F value | P value |
|---|---|---|
| Freeze-thaw cycle | 1.673 | 0.185 |
| Temperature | 0.953 | 0.467 |
| Storage time | 0.353 | 0.787 |

TABLE 3

Analysis Result II of Concentration Value of Complement Factor H

| Comparative value | F value | P value |
|---|---|---|
| Freeze-thaw cycle*Temperature | 0.592 | 0.888 |
| Freeze-thaw cycle*Storage time | 0.244 | 0.986 |
| Temperature*Storage time | 2.217 | 0.215 |
| Freeze-thaw cycle*Temperature*Storage time | 0.441 | 0.998 |

As can be seen from the analysis result I of the concentration values shown in Table 2, there are no significant difference in the results of samples with different freeze-thaw cycles, different temperatures, and different storage time detected by using the kit of the present invention, that is, the kit for detecting the concentration of complement factor H and the detection method provided by the present invention has the consistent detection results obtained under the influence of different freeze-thaw cycles, temperatures, and storage time, which indicates that the kit and detection method provided by the present invention have extremely low requirements on samples, with accurate detection results, which can meet the clinical test standards.

In order to further verify the accuracy and sensitivity of this kit, a multivariate analysis of variance was performed in the present application, the analysis results are shown in Table 2, there is no difference in the concentration values of complement factor H under the influence of the crossover factors of freeze-thaw cycles and temperature, freeze-thaw cycles and storage time, temperature and storage time, freeze-thaw cycle and temperature and storage time, ie, even if the sample is under the influence of multiple factors, the detection results obtained by the kit and method provided by the present application are still consistent, which further demonstrates that the kit for detecting the concentration of complement factor H and detection method provided by the present invention are suitable for sample detection under different conditions, with accurate detection results, which can fully meet the clinical test standards.

Test Example 3 Detection of Concentration of Complement Factor H in Samples with Different Concentrations Under the normal working conditions of the instrument, samples with known concentrations as shown in Table 4 were detected, each sample was repeatedly tested 10 times. The relative deviation between the mean value of measured results and the known concentration was only 1.0%. It can be seen that the kit provided by the present application can detect samples with a concentration range of 4.66-800 mg/L with accurate detection results, which can fully meet the clinical test standards.

TABLE 4

Concentration Sample Settings

| Number | Concentration |
|---|---|
| 1 | 4.66 |
| 2 | 10 |
| 3 | 30 |
| 4 | 60 |
| 5 | 100 |
| 6 | 130 |
| 7 | 160 |
| 8 | 190 |
| 9 | 220 |
| 10 | 250 |
| 11 | 280 |
| 12 | 300 |
| 13 | 350 |
| 14 | 400 |
| 15 | 500 |
| 16 | 600 |
| 17 | 650 |
| 18 | 680 |
| 19 | 700 |
| 20 | 720 |
| 21 | 740 |
| 22 | 760 |
| 23 | 780 |
| 24 | 800 |

Test Example 4 Determination of Kit Performance

The performance of the reagent I and reagent II in the kits prepared in Example 4-6 were evaluated to determine whether the kits complied with the relevant standards of the Clinical and Laboratory Standard Institute of America, that is, the CLSI standard. The specific operation was the same as in Test Example 1.

It was determined that the kit provided in the present application conforms to the relevant standards the Clinical and Laboratory Standard Institute of America, that is, the CLSI standard.

Test Example 5 Detection of Concentration of Complement Factor H in Samples Under Different Environmental Conditions The kit provided in Example 4 was used for the detection of concentration of complement factor H in this example. The specific detection method was the same as in Test Example 5.

According to the result values of the concentration of complement factor H, the analysis results were obtained as shown in Table 4 and Table 5.

TABLE 4

Analysis Result I of Concentration Value of Complement Factor H

| Comparative value | F value | P value |
|---|---|---|
| Freeze-thaw cycle | 1.673 | 0.185 |
| Temperature | 0.953 | 0.467 |
| Storage time | 0.353 | 0.787 |

TABLE 5

Analysis Result II of Concentration Value of Complement Factor H

| Comparative value | F value | P value |
|---|---|---|
| Freeze-thaw cycle*Temperature | 0.592 | 0.888 |
| Freeze-thaw cycle*Storage time | 0.244 | 0.986 |
| Temperature*Storage time | 2.217 | 0.215 |
| Freeze-thaw cycle*Temperature*Storage time | 0.441 | 0.998 |

As can be seen from the analysis result I of the concentration values shown in Table 4, there are no significant difference in the results of samples with different freeze-thaw cycles, different temperatures, and different storage time detected by using the kit of the present invention, that is, the kit for detecting the concentration of complement factor H and the detection method provided by the present invention has the consistent detection results obtained under the influence of different freeze-thaw cycles, temperatures, and storage time, which indicates that the kit and detection method provided by the present invention have extremely low requirements on samples, with accurate detection results, which can fully meet the clinical test standards.

In order to further verify the accuracy and sensitivity of this kit, a multi-factor analysis of variance was performed in the present application, the analysis results are shown in Table 5, there is still no difference in the concentration values of complement factor H under the influence of the crossover factors of freeze-thaw cycles and temperature, freeze-thaw cycles and storage time, temperature and storage time, freeze-thaw cycles and temperature and storage time, ie, even if the sample is under the influence of multiple factors, the detection results obtained by the kit and method provided by the present application are still consistent, which further demonstrates that the kit for detecting the concentration of complement factor H and the detection method provided by the present invention are suitable for sample detection under different conditions, with accurate detection results, which can fully meet the clinical test standards.

Test Example 6 Detection of Concentration of Complement Factor H in Samples with Different Concentration Under the normal working conditions of the instrument, samples with known concentrations as shown in Table 6 were measured, each sample was repeatedly measured 10 times. The relative deviation between the mean value of measured results and the known concentration was only 1.0%. It can be seen that the kit provided by the present application can detect samples with a concentration range of 4.66-800 mg/L with accurate detection results, which can fully meet the clinical test standards.

TABLE 6

Concentration Sample Settings

| Number | Concentration |
|---|---|
| 1 | 4.66 |
| 2 | 10 |
| 3 | 30 |
| 4 | 60 |
| 5 | 100 |
| 6 | 130 |
| 7 | 160 |
| 8 | 190 |
| 9 | 220 |
| 10 | 250 |
| 11 | 280 |
| 12 | 300 |
| 13 | 350 |
| 14 | 400 |
| 15 | 500 |
| 16 | 600 |
| 17 | 650 |
| 18 | 680 |
| 19 | 700 |
| 20 | 720 |
| 21 | 740 |
| 22 | 760 |
| 23 | 780 |
| 24 | 800 |

The present invention adopts Example 4 as a comparison basis to analyze the difference between the prior art and the present application.

Comparative Example 1

Figure 6:
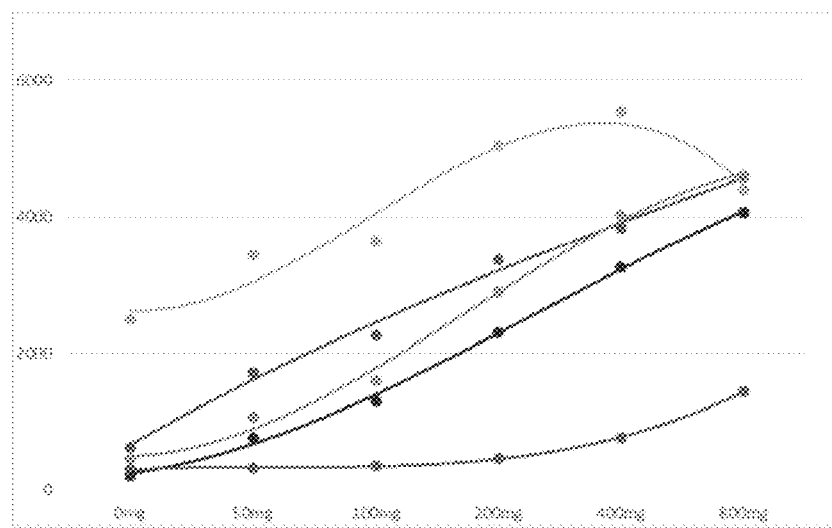
FIG. 6 is a graph showing the effect of the detection of complement factor H by different formula ingredients set in Example 4 of the present invention, observed at 100 mg, the curves in the figure are, from top to bottom: the detection result curve after replacing PEG200 of Example 4 with PEG6000, the detection result curve of complement factor H using the formula disclosed in CN102323427A in the background, the detection result curve of complement factor H after replacing the Tris buffer in Example 4 with phosphate, the detection result curve of Example 4, and the detection result curve of complement factor H after replacing PEG6000 in CN102323427A with PEG200.

The kit of Example 4 was used as a experimental group, the concentration of complement factor H detected by the formula after replacing PEG200 of Example 4 with PEG6000 as a kit for detecting complement factor H as CK1, the concentration of complement factor H detected by the formula disclosed in CN102323427A described in the background as a kit for detecting complement factor H as CK2, the concentration of complement factor H detected by the formula after replacing Tris buffer in Example 4 with phosphate as a kit for detecting complement factor H as CK3, and the concentration of complement factor H detected by the formula after replacing PEG6000 in CN102323427A with PEG200 as a kit for detecting complement factor H as CK4, the detection method was the same as steps 2 and 3 in Test Example 2, and the detection results as shown in FIG. 6 were obtained.

According to the detection results shown in FIG. 6, when the formula disclosed in CN102323427A is used as a kit for detecting complement factor H or the key reagent PEG6000 or phosphate buffer solution for detecting complement C1q is replaced with the PEG200 or Tris buffer of Example 4 of the present invention, respectively, for the detection of complement factor H, no good linear relationship could be obtained, which means that the CK1-4 cannot get a good test result, and their accuracy, repeatability, precision were all poor.

The present invention is characterized in that the method provided by the present invention has a wide detection range, and can detect the level of complement factor H in a concentration range of 4.86-2000 mg/l; with high detection efficiency and detection time of only 1 min, only takes 5-10 minutes for the entire detection process; has low requirements for the storage conditions of blood, and can detect the blood samples with a storage temperature of −80 to 37° C., stored for up to four weeks, or frozen and thawed within 4 cycles with detection results not affected, has no anticoagulation requirements for blood, and can detect EDTA or heparin anticoagulant samples.

After a large amount of experimental research and verification, the inventor overcomes the unknown technical difficulties encountered in the detection of complement factor H by immunoturbidimetry, and finally achieves an efficient and accurate detection of complement factor H, which makes the detection of complement factor H have the above characteristics.

The invention claimed is:

1. A method for determining a concentration of complement factor H, comprising:
preparing a kit comprising a reagent I and a reagent II containing a complement factor H antibody for determining a concentration of complement factor H in a sample to be detected; wherein, the reagent I consists of a Tris buffer and a polyethylene glycol 200 solution, and the reagent II consists of the polyethylene glycol 200 solution and a latex particle suspension of the complement factor H antibody;
adding the reagent I consisting of the Tris buffer and the polyethylene glycol 200 solution to the sample to be detected, incubating to obtain a first detection sample, and detecting to obtain a first absorbance value A1 of the sample to be detected; adding the reagent II containing the complement factor H antibody to the first detection sample, incubating to obtain a second detection sample, and detecting to obtain a second absorbance value A2 of the sample to be detected;
adding the reagent I consisting of the Tris buffer and the polyethylene glycol 200 solution to a standard sample, incubating to obtain a first detection standard, and detecting to obtain a first absorbance value B1 of the standard; adding the reagent II consisting of the polyethylene glycol 200 solution and the latex particle suspension of the complement factor H antibody to the first detection standard, incubating to obtain a second detection standard, and detecting to obtain a second absorbance value B2 of the standard; and
using the resulting first absorbance value A1 and the second absorbance value A2 of the sample to be detected and the first absorbance value B1 and the second absorbance value B2 of the standard sample to obtain the concentration level of the complement factor H in the sample to be detected.

2. The method according to claim 1, wherein the concentration of PEG200 solution in the reagent I is 50-90 g/L.

3. The method according to claim 1, wherein the concentration of PEG200 solution in the reagent II is 10-30 g/L.

4. The method according to claim 1, wherein the complement factor H antibody is derived from one of a goat anti-human complement factor H antibody, a rabbit anti-human complement factor H antibody or a mouse anti-human complement factor H antibody, and has a titer of 1:64-128.

5. A method for detecting a concentration of a complement factor H, comprising:
preparing a kit comprising a reagent I and a reagent II for detecting a concentration of the complement factor H in a sample to be detected; wherein, the reagent I consists of a Tris buffer and polyethylene glycol 400 solution, and the reagent II consists of a Tris buffer, PEG400 solution and a complement factor H antibody;
adding the reagent I consisting of the Tris buffer and the polyethylene glycol 400 solution to the sample to be detected, incubating to obtain a first detection sample, and detecting to obtain a first absorbance value A1 of the sample to be detected; adding the reagent II consisting of the Tris buffer, the complement factor H antibody and the polyethylene glycol 400 to the first detection sample, incubating to obtain a second detection sample, and detecting to obtain a second absorbance value A2 of the sample to be detected;
adding the reagent I consisting of the Tris buffer and the polyethylene glycol 400 to a standard sample, incubating to obtain a first detection standard, and detecting to obtain a first absorbance value B1 of the standard; adding the reagent II consisting of the Tris buffer, the serum anti-complement factor H antibody and the polyethylene glycol 400 to the first detection standard, incubating to obtain a second detection standard, and detecting to obtain a second absorbance value B2 of the standard; and
using the resulting first absorbance value A1 and the second absorbance value A2 of the sample to be detected and the first absorbance value B1 and the second absorbance value B2 of the standard to obtain the concentration level of the complement factor H in the sample to be detected.

6. The method according to claim 5, wherein the concentration of the PEG400 solution in the reagent I is 40-80 g/L.

7. The method according to claim 6, wherein the concentration of the PEG400 solution in the reagent II is 40-80 g/L, and a volume concentration of the serum anti-complement factor H antibody solution is 400-800 ml/L.

8. The method according to claim 1, wherein the using the resulting first absorbance value A1 and the second absorbance value A2 of the sample to be detected and the first absorbance value B1 and the second absorbance value B2 of the standard to obtain the concentration level of the complement factor H in the sample to be detected comprises:
dividing a difference between the second absorbance value A2 and the first absorbance value A1 of the sample to be detected by a difference between the second absorbance value B2 and the first absorbance value B1 of the standard to obtain a ratio K; and
multiplying the known concentration of the complement factor H in the standard sample by the resulting ratio K to obtain a concentration value of the complement factor H in the sample to be detected.

9. The method according to claim 1, wherein detection conditions set at the time of detection comprise a temperature of 37° C., a main wavelength of 546 nm or 600 nm, and a sub-wavelength of 700 nm.

10. The method according to claim 5, wherein complement factor H antibody is derived from one of a goat anti-human complement factor H antibody, a rabbit anti-human complement factor H antibody or a mouse anti-human complement factor H antibody, and has a titer of 1:64.

11. The method according to claim 5, wherein the using the resulting first absorbance value A1 and the second absorbance value A2 of the sample to be detected and the first absorbance value B1 and the second absorbance value B2 of the standard to obtain the concentration level of the complement factor H in the sample to be detected comprises:
dividing a difference between the second absorbance value A2 and the first absorbance value A1 of the sample to be detected by a difference between the second absorbance value B2 and the first absorbance value B1 of the standard to obtain a ratio K; and multiplying the known concentration of the complement factor H in the standard sample by the resulting ratio K to obtain a concentration value of the complement factor H in the sample to be detected.

12. The method according to claim 5, wherein detection conditions set at the time of detection comprise a temperature of 37° C., a main wavelength of 546 nm or 600 nm, and a sub-wavelength of 700 nm.

* * * * *